United States Patent [19]

Lutz

[11] 4,282,380
[45] Aug. 4, 1981

[54] REDUCTIVE ALKYLATION AND DEHALOGENATION OF M-NITROBENZYL HALIDES

[75] Inventor: Albert W. Lutz, Princeton, N.J.

[73] Assignee: American Cyanamid Company, Stamford, Conn.

[21] Appl. No.: 54,739

[22] Filed: Jul. 5, 1979

[51] Int. Cl.³ .................. C07C 85/08; C07C 85/24
[52] U.S. Cl. .................... 564/398; 564/406; 564/412
[58] Field of Search ............... 260/577; 564/398, 406, 564/412

[56] References Cited

U.S. PATENT DOCUMENTS

| 3,350,450 | 10/1967 | Dorell et al. | 260/577 |
| 3,541,153 | 11/1970 | Sandridge | 260/577 |
| 3,933,739 | 1/1976 | Wilder | 260/577 X |
| 4,078,001 | 3/1978 | Sommers | 260/577 |
| 4,085,141 | 4/1978 | Wedemeyer et al. | 260/570 X |
| 4,140,718 | 2/1979 | Symon | 260/577 X |

OTHER PUBLICATIONS

Sobolev et al. "Chemical Abstracts", vol. 54, p. 411b (1960).
Berezovskii et al."Chemical Abstracts", vol. 54, p. 8679e (1960).

*Primary Examiner*—Robert V. Hines
*Attorney, Agent, or Firm*—H. G. Jackson

[57] ABSTRACT

Substituted N-alkylated aromatic amines are produced by reductively alkylating and dehalogenating the corresponding m-nitrobenzyl halides with pressurized hydrogen in the presence of a ketone and a platinum catalyst.

5 Claims, No Drawings

REDUCTIVE ALKYLATION AND DEHALOGENATION OF M-NITROBENZYL HALIDES

This invention relates to certain novel reductive alkylation reactions, whereby substituted m-nitrobenzyl halides are reductively alkylated and dehalogenated in one step to the corresponding N-alkylated aromatic amines which are desirable as intermediates in the preparation of 3,4-disubstituted 2,6-dinitroaniline herbicides.

The aromatic amines produced by the process of the present invention are represented by formula (I) below:

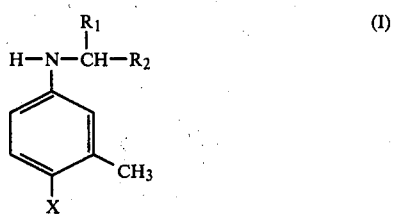

wherein X is alkyl $C_1$-$C_4$; $R_1$ and $R_2$ each are alkyl $C_1$-$C_4$ and may be the same or different.

The conventional route for the preparation of compounds of formula (I) from nitrobenzyl halides may be illustrated as follows:

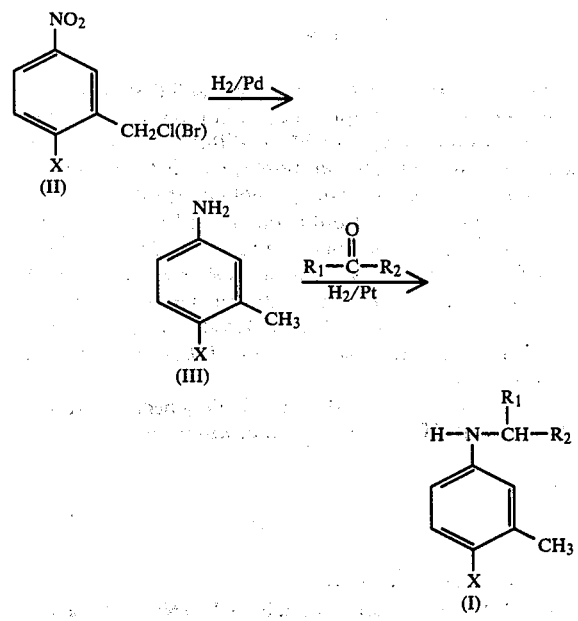

wherein X, $R_1$ and $R_2$ are as hereinbefore defined. Thus, a m-nitrobenzyl halide of formula (II) may be reduced and dehalogenated smoothly in one step with hydrogen and palladium as the catalyst, to yield compounds of formula (III). The above reaction may be carried out in the presence of inert solvents such as lower alcohols, e.g. ethanol, esters such as ethyl acetate and the like, at hydrogen pressures from atmospheric to about 100 psig., and at temperatures ranging from ambient to that of the boiling point of the selected solvent as determined by the pressure range of said reaction. Palladium is the catalyst of choice for this reaction since it is known in the art [e.g. *Catalytic Hydrogenation Over Platinum Metals,* by P. N. Rylander, Academic Press, N.Y., 1967, p. 405; and *Catalytic Hydrogenation,* by R. L. Augustine, Marcel Dekker, Inc., N.Y., 1965, p. 125] that it not only promotes bond cleavage but is also the least affected by the catalyst poisoning properties of the halide ions.

The next step in the above sequence, the reductive alkylation of a compound of formula (III) using palladium as the catalyst to prepare compounds of formula (I), cannot be carried out. In this reaction, the catalyst of choice is platinum, and its use allows the ready conversion of a compound of formula (III) to a compound of formula (I). These findings suggest that in the reaction sequence, illustrated above, two catalysts in two separate steps are required to prepare a compound of formula (I) from the corresponding compound of formula (II). Obviously, it would be more advantageous to convert a m-nitrobenzyl halide (II) to the desired N-alkyl aniline of formula (I) in one step and using only one catalyst.

It has now been found that the above nitrobenzyl halides (II) can be converted to the desired compounds of formula (I) in one step in the presence of a ketone, if the catalyst used is platinum. This one-step reductive alkylation and dehalogenation reaction is novel and unexpected considering that hitherto the use of platinum (and rhodium) as catalyst(s) was indicated for the reduction of compounds containing benzyl halogen when dehalogenation of such groups was to be minimized.

By the novel method of the present invention, the simultaneous dehalogenation and reductive alkylation of formula (II) m-nitrobenzyl halides may be conducted at the temperature range of from about 20° C. to about 100° C. in the presence of solvents such as ethyl acetate or lower alcohols such as ethanol, although the reaction may be carried out in the presence of excess ketone as solvent and reactant.

Illustrative ketones that may be used in the process of this invention include, for example, acetone, methyl ethyl ketone, diethyl ketone, 2-hexanone, 3-hexanone, methyl isobutyl ketone, and the like.

As stated above, the catalyst of choice is platinum. For use as catalyst, this metal is commercially available in a variety of forms, such as a finely dispersed powder, platinum on carbon, platinum on silica, platinum on diatomaceous earth, or on any other inert carrier. Of these, platinum on carbon support is most preferred, by reason of the fact that it is readily available from commercial sources.

Acid promoters such as p-toluenesulfonic acid or β-naphthalenesulfonic acid may be used, if so desired.

A typical procedure for practicing the reductive alkylation and dehalogenation of this invention is as follows.

A pressure vessel is charged with a m-nitrobenzyl halide of formula (II), the appropriate ketone, platinum on carbon catalyst, and if so desired an inert solvent selected from the group named above. An acid promoter may also be added, if so desired. The vessel is then sealed, and preferably deoxygenated by evacuation, followed by purging with purified nitrogen. The reactor is then pressurized to 10 to 80 psig., agitated and heated if desired, at the temperature range of from about 20° C. to about 100° C. Reaction periods of from 10 minutes to several hours, during which time the pressure in the vessel is either maintained by repressurizing with hydrogen gas, or allowed to decrease, are generally sufficient to insure completion of the reaction. Thereafter, the vessel is vented and opened and the contents removed. The product is worked up in a conventional manner.

The N-alkylated aromatic amines of formula (I) produced by the process of the present invention are useful as intermediates in the manufacture of the corresponding 2,6-dinitroaniline herbicides and bud growth regulators of Belgian Patents Nos. 787,939 and 785,584.

The present invention is further illustrated by the following examples, which are not to be taken as limitative thereof.

EXAMPLE 1

Preparation of 4-Ethyl-N-(1-ethylpropyl)-m-toluidine

A mixture of α-chloro-2-ethyl-5-nitrotoluene (5.0 g; 0.025 mol), diethyl ketone (30 ml) and 5% platinum on carbon catalyst (Pt/C; 0.50 g) is charged to a pressure vessel. Next, the vessel is sealed, evacuated and purged with nitrogen and is then pressurized with hydrogen gas to 40 to 60 psig. The reaction mixture is agitated until the theoretical amount of hydrogen is taken up (2.5 hours). The vessel is then vented, the reaction mixture diluted with methylene chloride and filtered. The filtrate is concentrated under vacuum to yield an off-white solid (6.1 g). This solid is dissolved in 0.5 N hydrochloric acid (200 ml) at 90° C. The aqueous solution is then cooled to room temperature, extracted with ether (3x) and made alkaline. An oil separates and is removed by extraction with ether. The ether phase is washed with water, dried and concentrated under vacuum to afford 3.82 g (74.5%) of crude product, a brown oil, found to be 73.7% pure by glc.

EXAMPLE 2

Preparation of N-Isopropyl-4-propyl-m-toluidine

By the procedure of Example 1, α-chloro-2-propyl-5-nitrotoluene is reacted with acetone to afford the desired title product.

EXAMPLE 3

Preparation of 4-Ethyl-N-(1-ethylpropyl)-2,6-dinitro-m-toluidine

A solution of 13.0 g of concentrated nitric acid, 10.75 g of concentrated sulfuric acid, and 4.88 g of water is added dropwise over a 2.3 hour period to a stirred solution of 4-ethyl-N-(1-ethylpropyl)-m-toluidine in 35 ml of 1,2-dichloroethane. The temperature of the mixture is maintained between 18° C. and 21° C. during the addition and for an additional 44 hours. The mixture is poured onto 30 g ice and then extracted with methylene chloride. The extracts are combined with the dichloroethane layer, the combined organic layers washed with 2.5% aqueous sodium hydroxide and water and dried over magnesium sulfate. The solution is evaporated to dryness under vacuum to yield a dark brown solid. Purification by chromatography affords the title product, melting point 51°–53° C.

Substituting N-isopropyl-4-propyl-m-toluidine for 4-ethyl-N-(1-ethylpropyl)-m-toluidine in the above reaction, N-isopropyl-4-propyl-2,6-dinitro-m-toluidine can be prepared.

We claim:

1. A process for the preparation of a compound of formula:

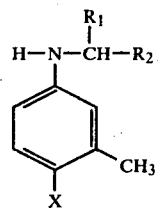

wherein $R_1$ and $R_2$ each are alkyl $C_1$–$C_4$ and may be the same or different; X is alkyl $C_1$–$C_4$, comprising: reductively alkylating and dehalogenating in one step a compound of formula:

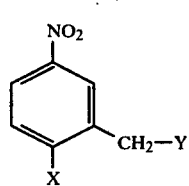

wherein Y is chlorine or bromine, and X is as hereinabove defined, by reacting same with an equimolar or excess amount of a ketone of formula:

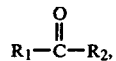

wherein $R_1$ and $R_2$ are as hereinabove defined, and with hydrogen used in the presence of platinum catalyst at a temperature ranging from 20° to 100° C. and at a pressure range of from 10 psig. to 80 psig.; for a period of time sufficient to essentially complete the reaction.

2. The process according to claim 1, wherein the platinum catalyst is dispersed over the surface of an inert support of carbon, silica or diatomaceous earth; and the process is carried out in the presence of an inert solvent of lower alcohols or ethyl acetate; and an acid promoter of p-toluenesulfonic acid or beta-naphthalenesulfonic acid.

3. The process according to claim 1, wherein $R_1$ and $R_2$ each are alkyl $C_1$–$C_2$; Y is chlorine; and the ketone

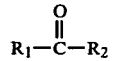

is used in excess over theory.

4. The process according to claim 1, wherein $R_1$ and $R_2$ each are ethyl; X is ethyl; Y is chlorine, the ketone is diethyl ketone used in excess over theory; the catalyst is platinum on carbon support; the temperature range is from 20° C. to 45° C., and the pressure range is from 30 psig. to 60 psig.

5. The process according to claim 1, wherein $R_1$ and $R_2$ each are methyl; X is n-propyl; Y is chlorine, the ketone is acetone used in excess over theory; the catalyst is platinum on carbon support; the temperature range is from 20° C. to 45° C., and the pressure range is from 30 psig. to 60 psig.